(12) United States Patent
Sendai

(10) Patent No.: US 7,453,979 B2
(45) Date of Patent: Nov. 18, 2008

(54) TOMOGRAPHIC IMAGE OBTAINMENT APPARATUS AND METHOD

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/925,058

(22) Filed: Oct. 26, 2007

(65) Prior Publication Data
US 2008/0101537 A1 May 1, 2008

(30) Foreign Application Priority Data
Oct. 26, 2006 (JP) ............... 2006-290746

(51) Int. Cl.
*A61B 6/00* (2006.01)
(52) U.S. Cl. .......................... 378/23; 378/37
(58) Field of Classification Search ............ 378/21–27, 378/37, 901; 382/130, 131, 132
See application file for complete search history.

(56) References Cited
U.S. PATENT DOCUMENTS
6,341,156 B1   1/2002   Baetz et al. ............... 378/98.8

2007/0086639 A1* 4/2007 Sakaida ..................... 382/132

FOREIGN PATENT DOCUMENTS
JP        2005-149762 A        6/2005

* cited by examiner

*Primary Examiner*—Courtney Thomas
(74) *Attorney, Agent, or Firm*—Sughrue Mion, PLLC

(57) ABSTRACT

When radiographic images are obtained by radiography using a tomographic image obtainment apparatus, the degree of overlap of anatomical structures of a subject is obtained. Further, a condition of exposure, such as angles θ of radiography, is changed based on the degree of overlap. The angles θ of radiography are angles at which a radiation irradiation unit performs radiography at a plurality of positions to obtain a plurality of radiographic images. The tomographic image obtainment apparatus produces a tomographic image by reconstructing the tomographic image from a plurality of radiographic images obtained by irradiating the subject with radiation from various directions.

9 Claims, 15 Drawing Sheets

FIG.15

DEGREE OF
OVERLAP

SMALL

| DENSITY | RANGE OF RADIOGRAPHY ANGLES | NUMBER OF TIMES OF RADIOGRAPHY |
|---|---|---|
| LEVEL 1 | ±10deg | 11 |
| LEVEL 2 (STANDARD) | ±15deg | 11 |
| LEVEL 3 | ±20deg | 11 |
| LEVEL 4 | ±30deg | 11 |

LARGE

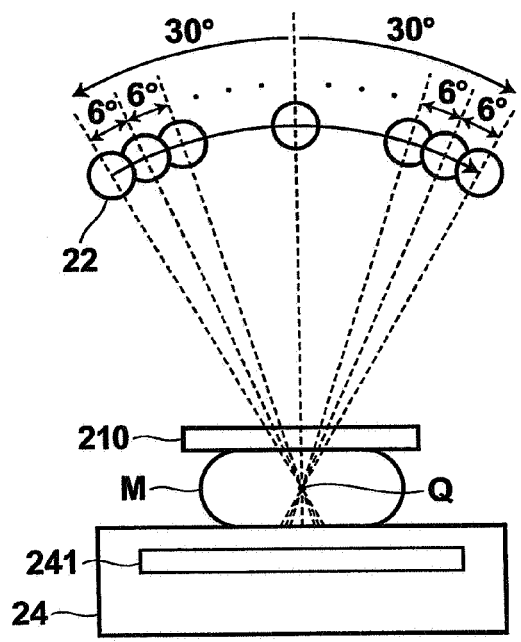
FIG.17A
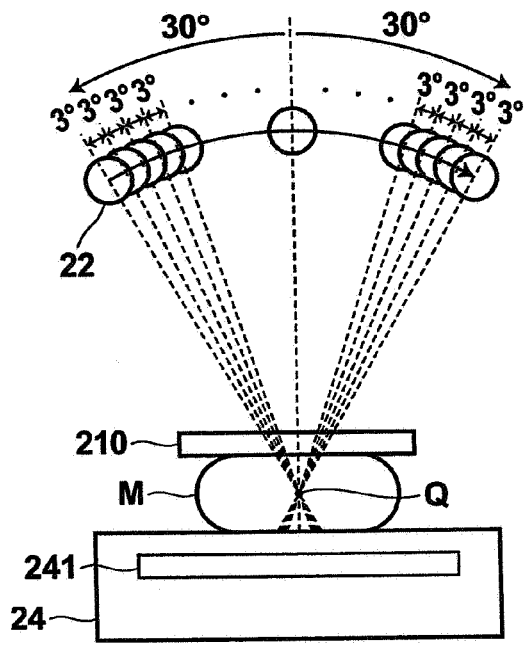
FIG.17B
FIG.18
DEGREE OF OVERLAP
SMALL ↓ LARGE
| DENSITY | RANGE OF RADIOGRAPHY ANGLES | NUMBER OF TIMES OF RADIOGRAPHY |
|---|---|---|
| LEVEL 1 | ±30deg | 11 |
| LEVEL 2 (STANDARD) | ±30deg | 17 |
| LEVEL 3 | ±30deg | 21 |
| LEVEL 4 | ±30deg | 31 |

DEGREE OF OVERLAP
SMALL ↓ LARGE

| DENSITY | RANGE OF RADIOGRAPHY ANGLES | NUMBER OF TIMES OF RADIOGRAPHY |
|---|---|---|
| LEVEL 1 | ±10deg | 11 |
| LEVEL 2 (STANDARD) | ±15deg | 17 |
| LEVEL 3 | ±20deg | 21 |
| LEVEL 4 | ±30deg | 31 |

| THICKNESS OF BREAST | RANGE OF RADIOGRAPHY ANGLES | NUMBER OF TIMES OF RADIOGRAPHY |
|---|---|---|
| ~ 20mm | ±10deg | 11 |
| 21mm ~ 40mm | ±15deg | 11 |
| 41mm ~ 60mm | ±20deg | 11 |
| 61mm ~ | ±30deg | 11 |

FIG.22

| WEIGHT OF BREAST | RANGE OF RADIOGRAPHY ANGLES | NUMBER OF TIMES OF RADIOGRAPHY |
|---|---|---|
| ~ 300g | ±10deg | 11(11) |
| 301g ~ 600g | ±15deg | 11(17) |
| 601g ~ 900g | ±20deg | 11(21) |
| 900g ~ | ±30deg | 11(31) |

TOMOGRAPHIC IMAGE OBTAINMENT APPARATUS AND METHOD

BACKGROUND OF THE INVENTION

1. Field of the Invention

The present invention relates to a tomographic image obtainment apparatus and method for obtaining a tomographic image by radiography.

2. Description of the Related Art

In recent years, tomosynthesis radiography (tomosynthesis) has also been proposed in the field of X-ray radiography apparatuses (CR: computed radiography) to observe diseased parts in more detail. In tomosynthesis, an X-ray tube is moved and the subject is irradiated with X rays at various angles to obtain radiographic images of the subject. Then, the obtained radiographic images are added together to obtain a tomographic image (a cross-sectional image or a slice image) in which the state of the subject on a desired cross-sectional plane of the subject is emphasized.

In tomosynthesis radiography, a subject is radiographed at various angles of radiography (photography) by moving an X-ray tube parallel to a detector, such as a flat panel, or by moving the X-ray tube in a circle or in an ellipse. Accordingly, a plurality of radiographic images are obtained, and a tomographic image is reconstructed from the plurality of radiographic images. The tomographic image may be obtained by moving the plurality of radiographic images parallel to each other, by adjusting the sizes of the radiographic images and by adding the radiographic images together. Further, the radiographic images are obtained, as digital images, using digital-type solid-state detectors arranged in matrix form so that operations among the radiographic images are easily performed.

When a subject is irradiated with radiation a plurality of times to perform tomosynthesis radiography, if the dose of each radiation is the same as that of radiation in ordinary radiography, the subject is exposed to a large dose of radiation in total. Therefore, when the subject is irradiated with radiation a plurality of times, the dose of each radiation is reduced as the number of times of radiation increases. However, the specification of a detector that is used in an X-ray radiography apparatus is determined so that high quality images are obtained when radiography is performed at high dose values by assuming that the detector is used for ordinary X-ray radiography. Therefore, if radiographic images are obtained at extremely low doses, artifacts tend to appear. The artifacts have stripe patterns extending in a direction vertical or horizontal to the arrangement direction of the digital-type solid-state detectors, which are arranged in matrix form.

When a tomographic image is obtained by tomosynthesis, radiographic images are moved parallel to each other or the sizes of the radiographic images are adjusted. Further, the radiographic images are added to obtain the tomographic image. However, if the radiographic images are obtained by a digital-type solid-state area detector that is set parallel to the direction of the X-axis of a bed (table) for placing a subject and the obtained radiographic images are added, the aforementioned artifacts, which have the vertical or horizontal stripe patterns, appear at the same position and superposed one on another in some cases. In such cases, the artifacts are emphasized.

Therefore, a method for preventing vertical or horizontal stripe-shaped detector defects from appearing at the same position has been proposed (for example, U.S. Pat. No. 6,341,156 or the like). In this method, formation of artifacts is prevented by inclining the detector by angle α with respect to the direction of the X-axis of a bed (table) on which a subject is placed.

Further, when radiographic images are obtained, a tube voltage and a tube electric current (tube current) are adjusted to obtain radiographic images that have appropriate contrast. However, since an appropriate tube voltage and an appropriate tube current differ depending on the size of a subject, setting is changed for each patient. Further, it is desirable that the tube voltage and the tube current are also appropriately adjusted when radiography is performed using a CT (computed tomography apparatus) for obtaining tomographic images. Therefore, a method for setting, based on the transmittance of radiation at a region to be observed, a tube voltage and a tube current that are appropriate for a patient has been proposed (for example, Japanese Unexamined Patent Publication No. 2005-149762 or the like). In this method, first, a two-dimensional radiographic image of the patient is obtained, and the transmittance of radiation at the region to be observed, which is in the obtained two-dimensional radiographic image, is used to set the tube voltage and the tube current.

Conventionally, when tomographic images are obtained by tomosynthesis radiography, even if the shapes or sizes of subjects differ from each other, radiography is performed without changing a radiation irradiation angle (photography angle or radiography angle or irradiation angle) at which a subject is irradiated with radiation and the number of times of irradiation in many cases. In tomosynthesis radiography, the subject is irradiated with radiation from various directions, and a distance from a radiation source to the subject differs depending on the radiation irradiation angle. Therefore, a region, of which a clear image is obtained, differs depending on the radiation irradiation angle, at which the subject is irradiated.

SUMMARY OF THE INVENTION

In view of the foregoing circumstances, it is an object of the present invention to provide a technique for changing the condition of exposure (radiography or photography) so that the most appropriate image of a subject is obtained when tomosynthesis radiography is performed on the subject.

A tomographic image obtainment apparatus according to the present invention is a tomographic image obtainment apparatus, wherein a tomographic image is reconstructed from a plurality of radiographic images obtained by irradiating a subject with radiation from various directions, the apparatus comprising:

a radiation image detector for obtaining radiographic images of the subject;

a radiation irradiation unit placed so as to face the radiation image detector, the radiation irradiation unit moving to a plurality of positions and irradiating, at the plurality of positions, the subject placed on the radiation image detector with radiation from various directions;

an overlap-degree obtainment means for obtaining the degree of overlap of anatomical structures of the subject; and an exposure condition setting means for setting, based on the degree of overlap obtained by the overlap-degree obtainment means, a condition of exposure by the radiation irradiation unit at the plurality of positions to obtain the plurality of radiographic images.

Further, a tomographic image obtainment method according to the present invention is a tomographic image obtainment method, wherein a tomographic image is reconstructed from a plurality of radiographic images obtained by irradiating a subject with radiation from various directions, the method comprising the steps of:

obtaining the degree of overlap of anatomical structures of the subject in a direction of irradiation; and setting a condition of exposure of the subject based on the obtained degree of overlap.

The term "anatomical structures" refers to tissues or internal organs of human bodies. Further, the phrase "the degree of overlap of anatomical structures" refers to "the degree of overlap of the tissues or internal organs".

Further, the term "a condition of exposure" (exposure condition) includes conditions, such as the range of radiography angles, radiation doses and intervals of radiography when a subject is radiographed from a plurality of positions.

Further, it is desirable that the overlap-degree obtainment means obtains the degree of overlap of the anatomical structures in the direction of the normal of a detection surface of the radiation image detector.

Further, the exposure condition setting means may set the condition of exposure so that the range of movement of the radiation irradiation unit is increased if the degree of overlap is large.

Further, the exposure condition setting means may set the condition of exposure so that an interval between the plurality of positions to which the radiation irradiation unit moves is reduced (narrowed) if the degree of overlap is large.

Further, the overlap-degree obtainment means may obtain the degree of overlap based on the pixel values of a radiographic image obtained by radiographing the subject on the radiation image detector.

Further, the tomographic image obtainment apparatus may further include an ultrasound image obtainment unit for obtaining an ultrasound image of the subject on the radiation image detector, and the overlap-degree obtainment means may obtain the degree of overlap based on the pixel values of the ultrasound image of the subject on the radiation image detector.

Further, the overlap-degree obtainment means may obtain the degree of overlap based on the thickness of the subject.

Further, the overlap-degree obtainment means may obtain the degree of overlap based on the weight of the subject.

According to the present invention, the degree of overlap of anatomical structures, such as tissue or internal organs, of a subject to be radiographed is obtained. Further, a condition of exposure, such as a radiography angle, interval of radiography and radiation dose, is set based on the obtained degree of overlap when tomosynthesis radiography is performed by the radiation irradiation unit. Therefore, it is possible to obtain radiographic images based on the characteristics of regions to be radiographed and to produce a tomographic image that is appropriate for diagnosis.

Further, since the degree of overlap in the direction of the normal of a detection surface of the radiation image detector is obtained, information about a direction in which the radiation is positioned at the center of the irradiation range can be obtained. Therefore, it is possible to obtain an appropriate condition of exposure.

Further, since the range of movement of the radiation irradiation unit is increased if the degree of overlap is large, it is possible to obtain detailed information about an area close to the edge of a radiography table, which is far from the center of the radiography table.

Further, since an interval of radiography performed by the radiation irradiation unit, which moves and performs radiography, is reduced if the degree of overlap is large, it is possible to obtain detailed information based on radiographic images obtained at narrow intervals.

Further, since the degree of overlap is obtained based on the pixel values of a radiographic image obtained by radiographing the subject on the radiation image detector, it is possible to accurately obtain the degree of overlap of the anatomical structures of the subject.

Further, since the degree of overlap is obtained based on the pixel values of an ultrasound image of the subject on the radiation image detector, it is possible to accurately obtain the degree of overlap of the anatomical structures of the subject. Further, it is possible to reduce the dose of radiation to which the subject is exposed.

Further, the degree of overlap may be obtained based on the thickness of the subject or the weight of the subject. In such a case, it is possible to accurately obtain the degree of overlap by a simple method without causing the subject to be exposed to radiation.

BRIEF DESCRIPTION OF THE DRAWINGS

FIG. 15 is an example of a table showing correspondences between the degrees of overlap and radiography angles;

FIG. 17A is a diagram illustrating intervals of radiography of the radiation source;

FIG. 17B is a diagram illustrating intervals of radiography of the radiation source;

FIG. 18 is an example of a table showing correspondences between the degrees of overlap and the numbers of times of radiography;

FIG. 22 is an example of a table showing correspondences between the ranges of radiography angles and the intervals of radiography.

DESCRIPTION OF THE PREFERRED EMBODIMENTS

Hereinafter, embodiments of the present invention will be described in detail with reference to the attached drawings. In the present embodiment, a tomographic image obtainment apparatus for obtaining a tomographic image (mammogram) of a breast in a compressed state will be described. The tomographic image obtainment apparatus for obtaining the tomographic image of the breast is a mammography apparatus for radiographing a breast in a compressed state by placing the breast on a radiography table (photography table). The tomographic image obtainment apparatus has a function for performing tomosynthesis radiography, and the breast is compressed with a breast compression plate.

Figure 1:
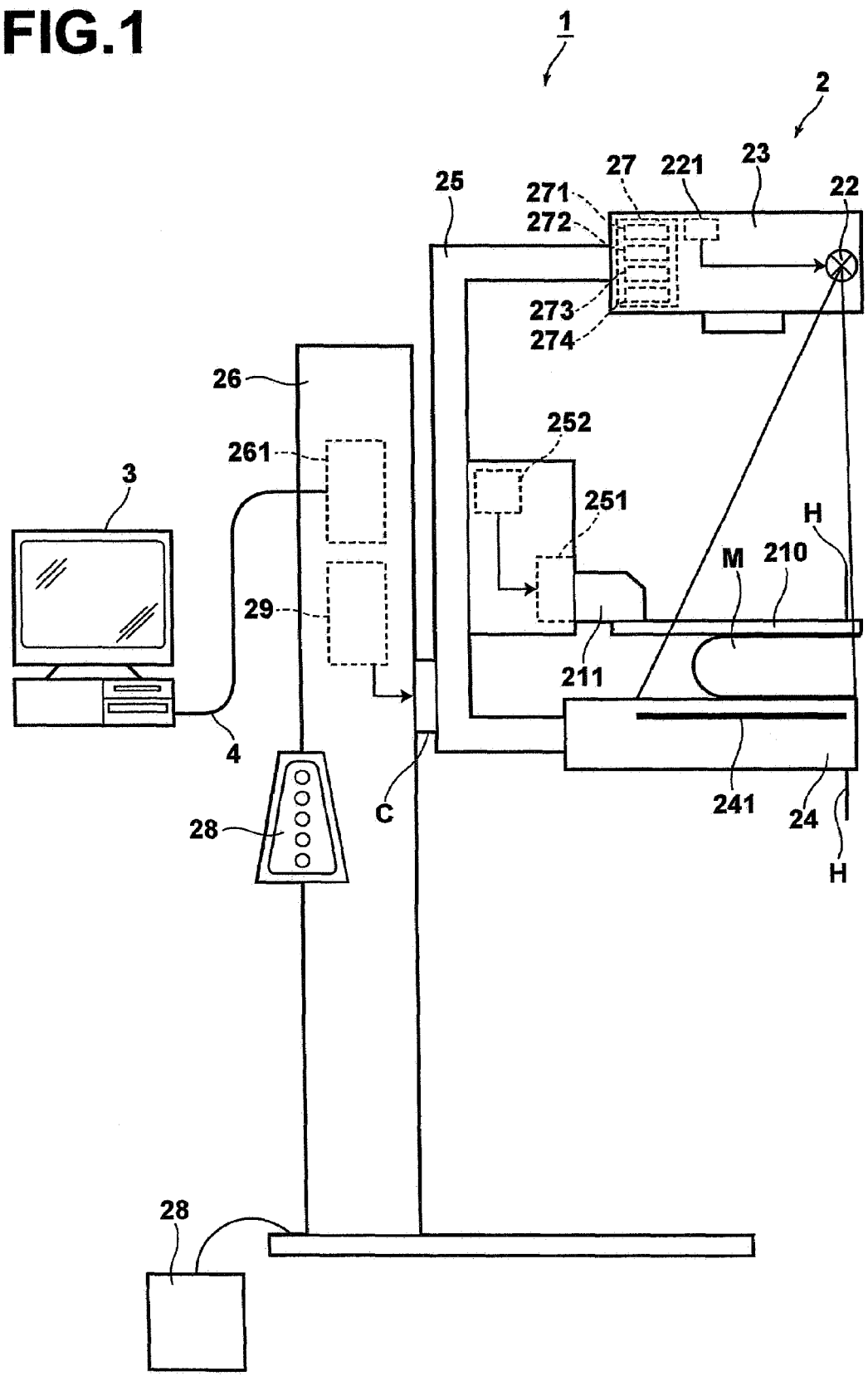
FIG. 1 is a diagram illustrating the configuration of a tomographic image obtainment apparatus in the first embodiment of the present invention.
Figure 2:
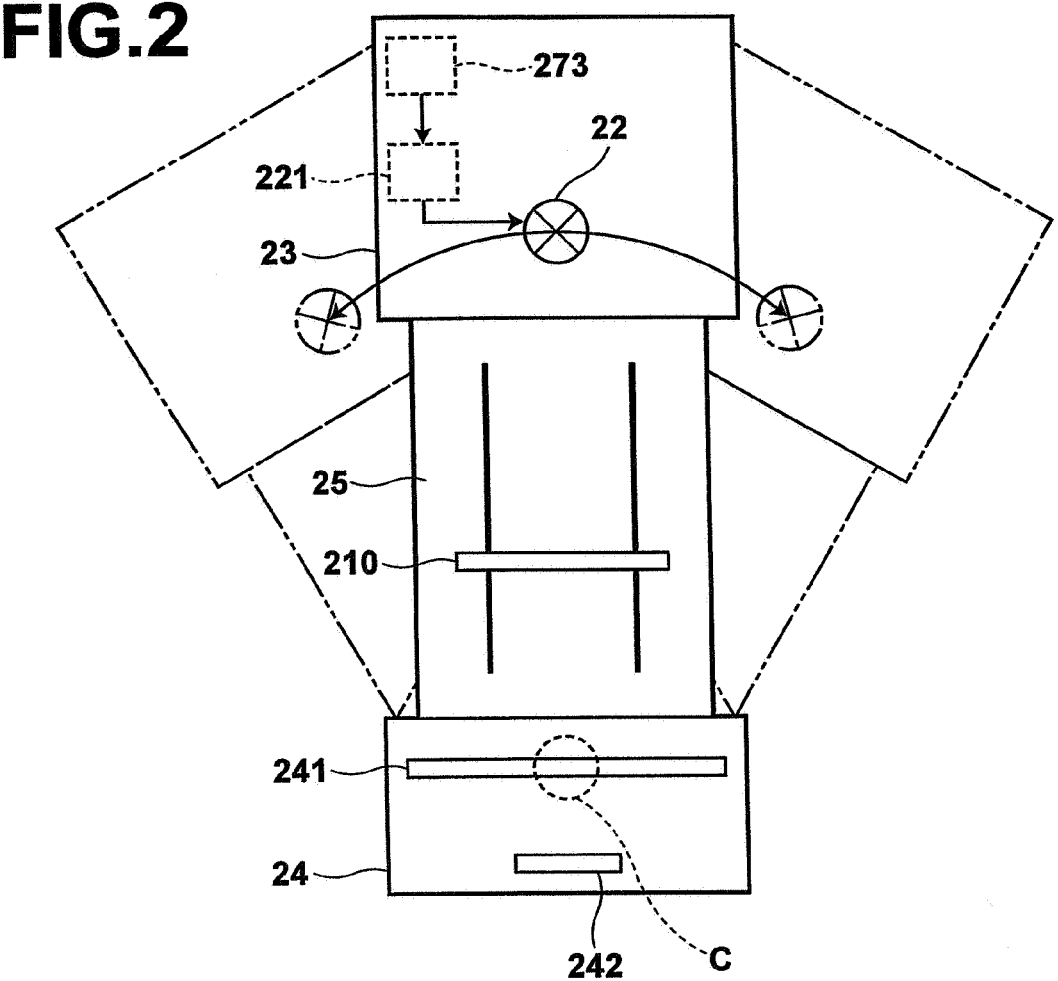
FIG. 2 is a frontal view of an arm of a mammography apparatus.

FIG. 1 is a diagram illustrating the configuration of a tomographic image obtainment apparatus according to the present invention. FIG. 2 is a frontal view of an arm of a mammography apparatus included in the tomographic image obtainment apparatus.

A tomographic image obtainment apparatus 1 includes a mammography apparatus 2, a tomographic image formation apparatus 3 and a network 4. The mammography apparatus 2 obtains a plurality of radiographic images (mammograms) of a breast of a subject by irradiating the breast with radiation from various directions to radiograph the breast. The tomographic image formation apparatus 3 produces a tomographic image by reconstructing the tomographic image from the plurality of radiographic images obtained by the mammography apparatus 2. The network 4 connects the mammography apparatus 2 and the tomographic image formation apparatus 3.

The mammography apparatus 2 includes a radiation storage unit 23, a radiography table 24, an arm 25, a base 26, a control unit 27 and a transmission unit 261. The radiation storage unit 23 stores a radiation irradiation unit (hereinafter referred to as a radiation source) 22 therein. The radiography table 24 stores a radiation image detector 241, such as a flat panel detector, therein, and the radiation image detector 241 is held in a recording medium holding unit, such as a cassette. The arm 25 connects the radiation storage unit 23 and the radiography table 24 so that they face each other. The arm 25 is attached to the base 26 by shaft C. The control unit 27 controls the radiation storage unit 23. The transmission unit 261 sends data, such as radiographic images obtained by radiography, to the tomographic image formation apparatus 3 through the network 4.

The base 26 further includes an operation unit 28 and an arm movement means 29. The operation unit 28 is used by an operator to adjust the height, rotation amount and direction of the arm 25. The arm movement means 29 moves the arm 25 based on an input at the operation unit 28. The arm movement means 29 moves the arm 25 up and down and rotates the arm 25 based on the input.

Further, the arm 25 includes an attachment unit 251 for attaching a compression plate 210 and a compression plate movement means 252. The attachment unit 251 and the compression plate movement means 252 are provided between the radiation storage unit 23 and the radiography table 24. The compression plate 210 compresses breast M of a subject by pressing the breast M from the upside against the radiography table 24. The compression plate movement means 252 moves the attachment unit 251 up and down in the vertical direction of the arm 25.

Further, the compression plate 210 includes an insertion portion 211 for inserting the compression plate 210 into the attachment unit 251.

The radiation storage unit 23 stores the radiation source 22 therein, and a radiation source movement means 221 is further provided. As illustrated in FIG. 2, the radiation source movement means 221 moves the radiation source 22 by rotating the radiation storage unit 23 with respect to the shaft C. The radiation source 22 is moved in an arc along a side of the radiography table 24, the side extending toward chest wall H of the subject (normally, the side is a longer side of the radiography table 24, which has a rectangular shape) (please refer to FIG. 3).

The radiation source 22 moves in an arc and irradiates breast M mounted on the radiography table 24 with radiation at various radiography angles. The radiation source 22 irradiates the breast M from each position of S1, S2, . . . , Sn. Further, when the breast M is radiographed, the breast M is placed on the radiography table 24 and compressed from the upside by the compression plate 210. Therefore, when the breast M is radiographed, the thickness of the breast M is approximately 4 to 5 cm. Therefore, for the purpose of obtaining an appropriate image for observing the breast M, it is desirable that the radiation source 22 emits radiation at each position so that the radiation is directed to point Q (hereinafter, referred to as an irradiation point). The point Q is a point that is approximately 2 cm higher than the vicinity of the center of the radiography surface of the radiography table 24 (specifically, the vicinity of the center of the radiography surface is the position of the center of the breast M when the breast M is placed on the upper surface of the radiography table 24).

Further, as illustrated in FIG. 2, a flat panel detector 241 and a dose detector 242 are provided in the radiography table 24. The flat panel detector 241 records image information based on the dose of radiation that has passed through the breast M by irradiation with radiation. Further, the flat panel detector 241 outputs image data representing the recorded image information. The dose detector 242 is provided under the flat panel detector 241. The dose detector 242 detects the dose of radiation that has been emitted from the radiation storage unit 23 and passed through the breast M.

Further, the shaft C, which is the center of rotation, is attached to the central position of the flat panel detector 241 so that the rotation center of the arm 25 becomes the same as the center of the flat panel detector 241. Further, the arm 25 is attached to the base 26 (please refer to FIG. 2).

In the present embodiment, the structure of the radiography table 24, in which the radiation image detector 241 is a flat panel detector, will be described below with reference to FIGS. 4 through 7.

Figure 4:
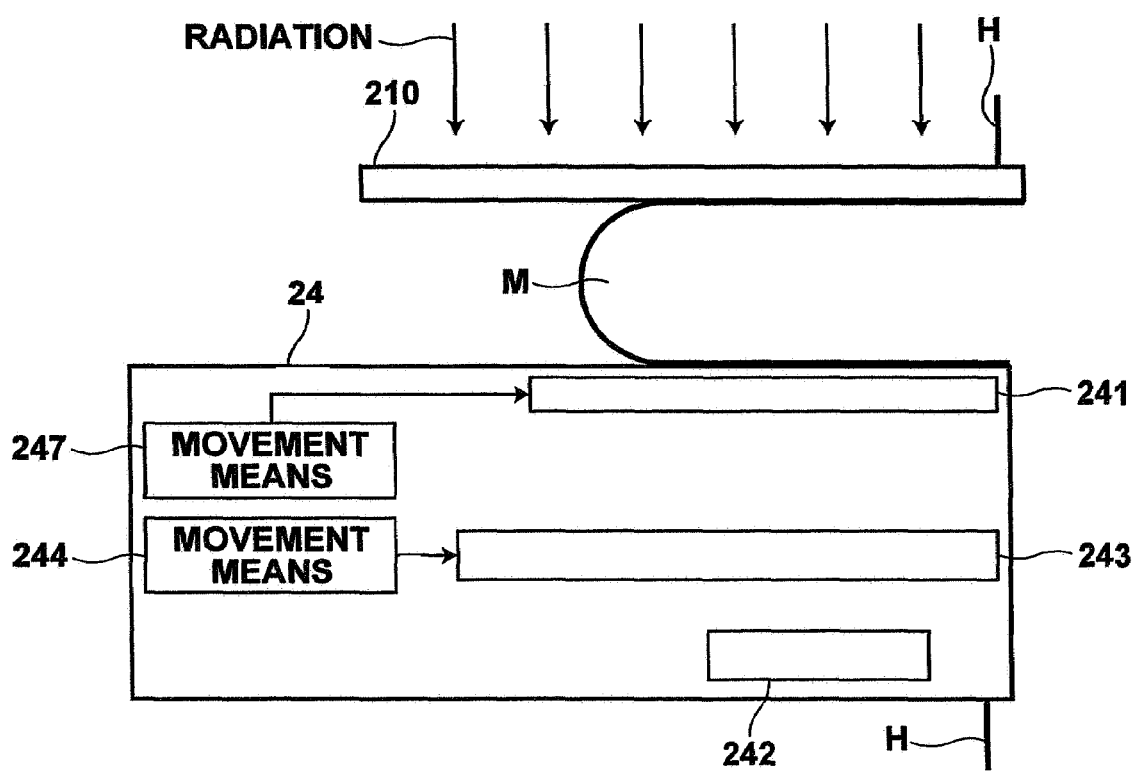
FIG. 4 is a diagram illustrating a relationship between a compression plate, a solid-state detector and a dose detector, the solid-state detector and the dose detector placed in a radiography table (No. 1)
Figure 5:
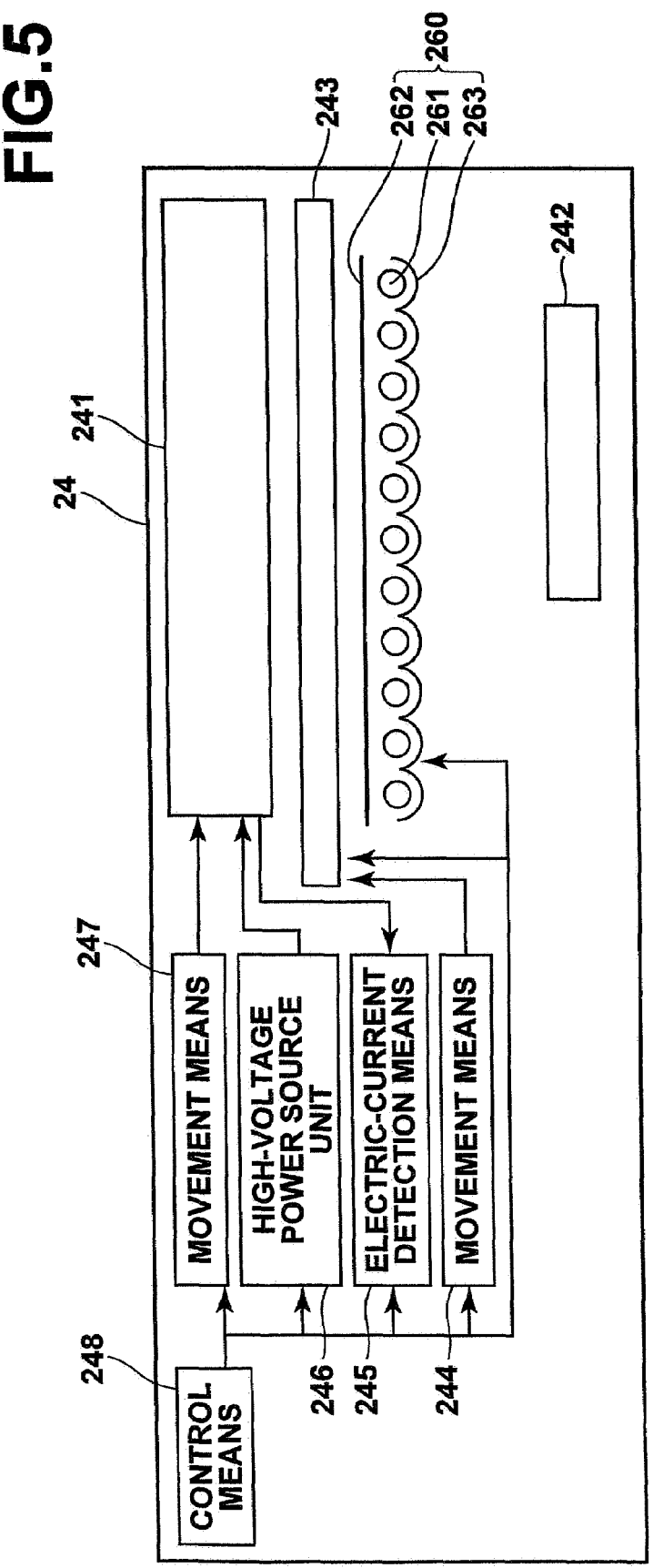
FIG. 5 is a schematic diagram illustrating the inside of the radiography table of the mammography apparatus.

As illustrated in FIGS. 4 and 5, in the radiography table 24, an exposure light source unit 243 for readout, an exposure-light-source-unit-for-readout movement means 244, an electric current detection means 245, a high-voltage power source unit 246, a pre-exposure light source unit 260, a radiation-image-detector movement means 247, and a control means for controlling the exposure light source unit 243 for readout, the electric current detection means 245, the high-voltage power source unit 246, the pre-exposure light source unit 260 and the movement means 247 and 244 are arranged. The exposure light source unit 243 for readout is used to read out image information recorded in the radiation image detector 241. The exposure-light-source-unit-for-readout movement means 244 moves the exposure light source unit 243 for readout in a sub-scan direction. The electric current detection means 245 obtains an image signal by detecting an electric current flowing out of the radiation image detector 241 when the exposure light source unit 243 for readout performs scan exposure on the radiation image detector 241. The high-voltage power source unit 246 applies a predetermined voltage to the radiation image detector 241. The pre-exposure light source unit 260 irradiates the radiation image detector 241 with pre-exposure light before starting radiography. The radiation-image-detector movement means 247 moves the radiation image detector 241 within the radiography table 24 in a direction approaching the chest wall H of a subject or in a direction (the sub-scan direction) moving away from the chest wall H of the subject.

Figure 6:
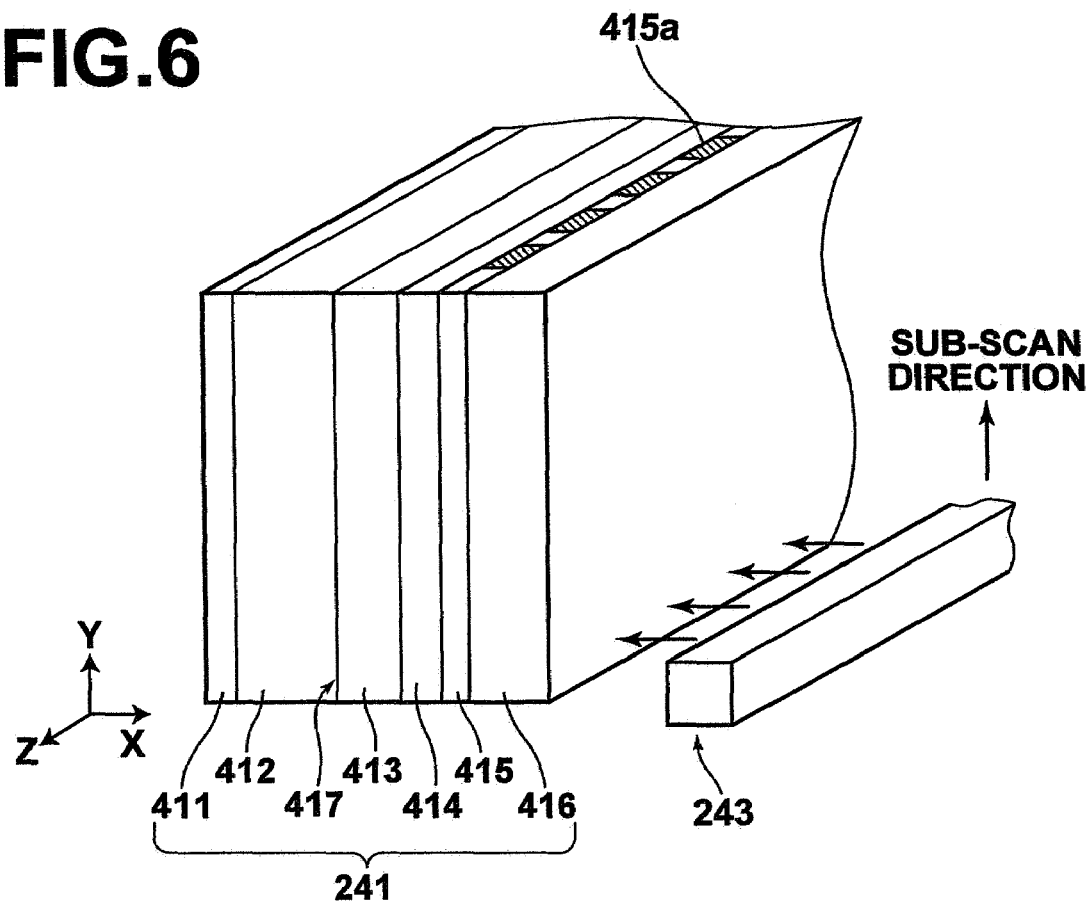
FIG. 6 is a schematic diagram illustrating a radiation image detector (solid-state detector)

The radiation image detector 241 is a solid-state detector adopting both a direct conversion method and a light readout method. The radiation image detector 241 records image information as a static latent image by being irradiated with record light that carries the image information. Further, the radiation image detector 241 generates an electric current corresponding to the static latent image by being scanned with readout light. Specifically, as illustrated in FIG. 6, the radiation image detector 241 is formed on a glass substrate 416. In the radiation image detector 241, a first conductive layer 411, a photoconductive layer 412 for recording, a charge transfer layer 413, a photoconductive layer 414 for readout and a second conductive layer 415 are superposed one on another in this order. The first conductive layer 411 transmits radiation passed through breast M (hereinafter, the radiation passed through the breast M is referred to as recording light). The photoconductive layer 412 for recording generates an electric charge by irradiation with the recording light and exhibits conductivity. The charge transfer layer 413 substantially acts as an insulator with respect to a latent-image polarity electric charge charged in the first conductive layer 411 and substantially acts as a conductor with respect to transfer polarity electric charge, of which the polarity is opposite to that of the latent-image polarity electric charge. The photoconductive layer 414 for readout generates an electric charge by irradiation with the readout light and exhibits conductivity. The second conductive layer 415 transmits the readout light. Further, a charge storage portion (a charge accumulation portion) 417 is formed at the interface between the photoconductive layer 412 for recording and the charge transfer layer 413.

Each of the first conductive layer 411 and the second conductive layer 415 forms an electrode. The electrode of the first conductive layer 411 is a flat-plate electrode, which is two-dimensional and flat. The electrode of the second conductive layer 415 is a stripe electrode, as illustrated with shading in FIG. 6 (please refer to a static electricity recording body disclosed in Japanese Unexamined Patent Publication No. 2000-105297). In the stripe electrode, a multiplicity of elements (linear electrodes) 415a for detecting recorded image information as image signals are arranged so that stripes are formed at pixel pitch. The arrangement direction of the elements 415a corresponds to a main scan direction, and the longitudinal direction of the elements 415a corresponds to a sub-scan direction.

The size of the radiation image detector (solid-state detector) 241 is 30 cm (longitudinal side)×24 cm (shorter side) so as to cope with large breasts. The solid-state detector 241 is accommodated in the radiography table 24 in such a manner that the longitudinal side of the solid-state detector 241 is placed in the main scan direction and the shorter side of the solid-state detector 241 is placed in the sub-scan direction.

As the exposure light source unit 243 for readout, a light source unit including a line light source and an optical system is used. In the line light source, a plurality of LED chips are arranged in a line, and the optical system linearly irradiates the solid-state detector 241 with light emitted from the light source. The exposure light source unit 243 for readout exposes the entire surface of the solid-state detector 241 to light by scanning the solid-state detector 241 in the longitudinal direction of the stripe electrodes 415a of the solid-state detector 241, in other words, in the sub-scan direction. The exposure light source unit 243 for readout is moved by the movement means 244 that is formed by a linear motor and scans the solid-state detector 241, keeping a necessary distance from the solid-state detector 241. Further, the exposure light source unit 243 for readout and the movement means 244 form a readout light scan means.

Figure 7:
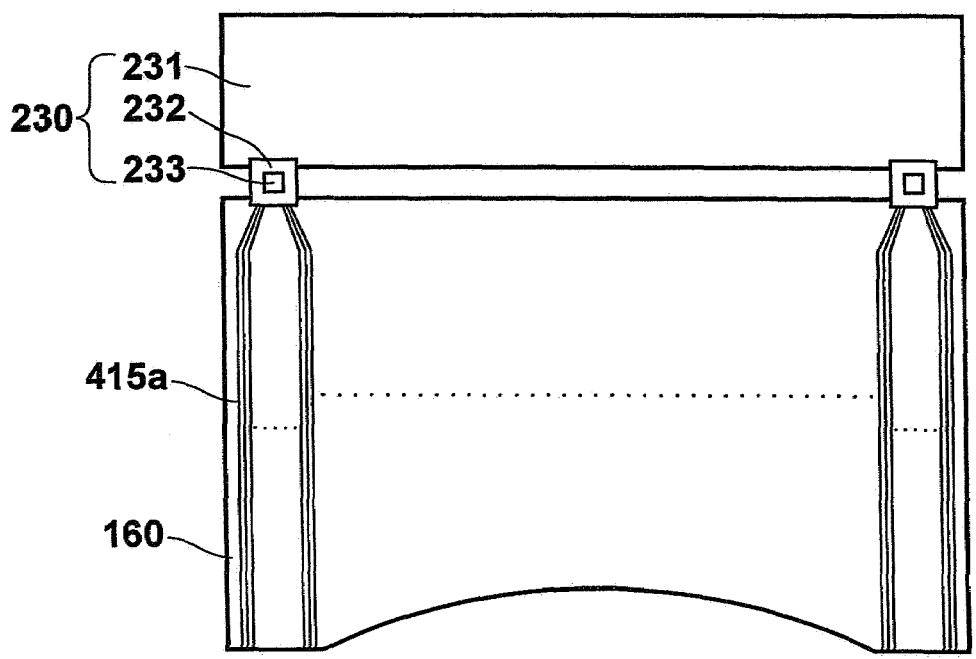
FIG. 7 is a diagram illustrating the connection between the radiation image detector and an electric current detection means.

FIG. 7 is a diagram illustrating connection between the solid-state detector 241 and the electric current detection means 245. As illustrated in FIG. 7, each element 415a of the solid-state detector 241 is connected to a charge amplifier IC 233 through a print pattern (not illustrated) formed on a TAB (Tape Automated Bonding) film 232 in the vicinity of an area contacting with chest wall H of a patient (a person to be examined). Further, the charge amplifier IC 233 is connected with a printed circuit board 231 through a print pattern (not illustrated) formed on the TAB film 232. In the present embodiment, not all elements 415a are connected to the same charge amplifier IC 233. Instead, a few charge amplifier IC's 233 or some tens of charge amplifier IC's 233 are provided in total and approximately a few elements 415a or a hundred of elements 415a that are adjacent to each other are sequentially connected to each of the charge amplifier IC's 233.

The electric current detection means 245 is not limited to the aforementioned embodiment, and it is not necessary that the charge amplifier IC's 233 are formed on the TAB film. The charge amplifier IC's 233 may be formed on the glass substrate 416 (a so-called COG (Chip on Glass) method).

Figure 8:
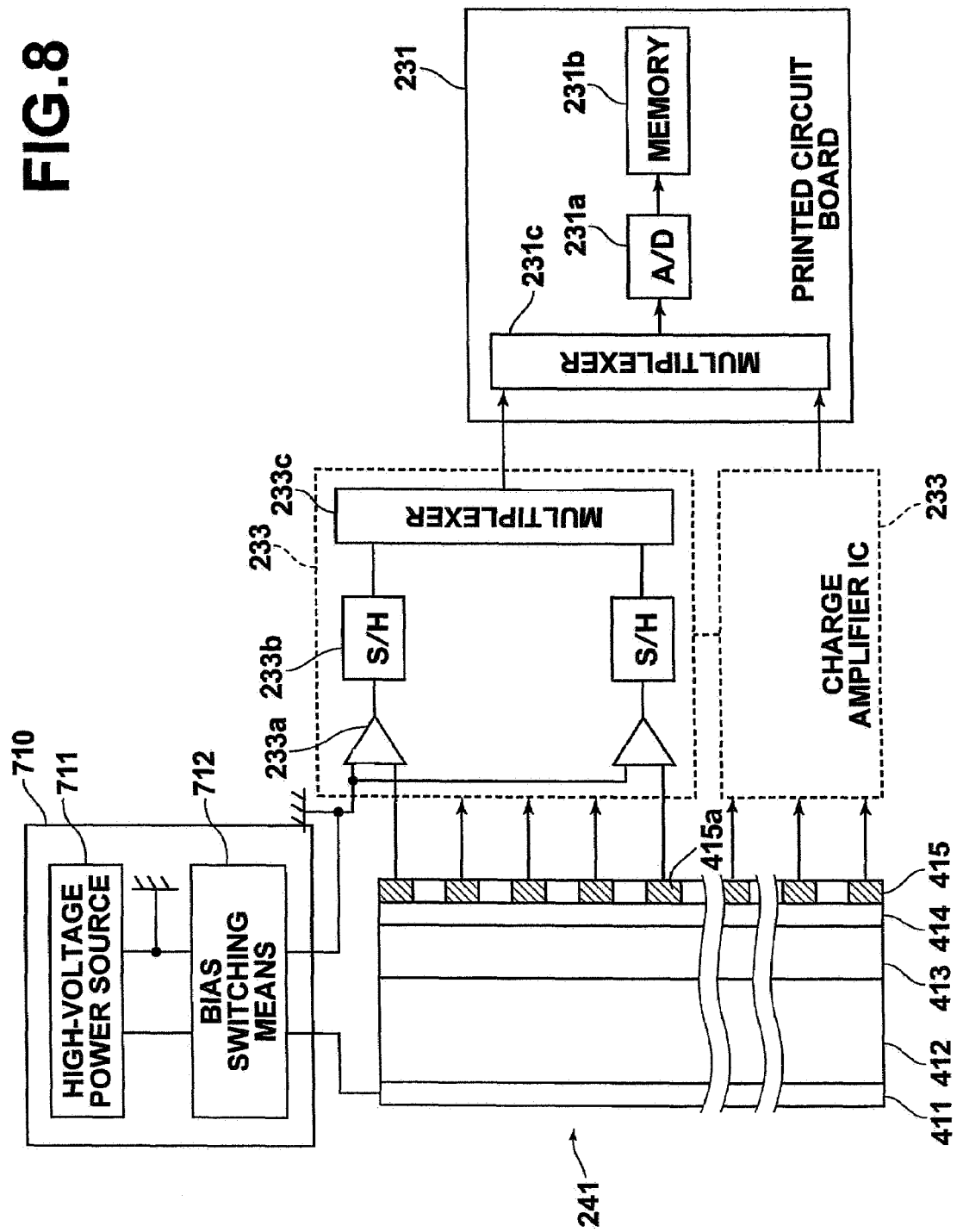
FIG. 8 is a block diagram illustrating the electric current detection means and a high-voltage power source unit in detail and the connection between the electric current detection means, the high-voltage power source unit and the solid-state detector.

FIG. 8 is a block diagram illustrating the electric current detection means 245 and a high-voltage power source unit 710, provided in the radiography table 24, in detail and connection of the electric current detection means 245 and the high-voltage power source unit 710 to the solid-state detector 241.

The high-voltage power source unit 710 is a circuit in which a high-voltage power source 711 and a bias switching means 712 are integrated with each other. The high-voltage power source 711 is connected to the static electricity recording unit (solid-state detector) 241 through the bias switching means 712 so that bias application/short-circuiting or the like to the solid-state detector 241 can be switched. This circuit is designed to prevent charge/discharge excessive electric current. The charge/discharge excessive electric current is prevented by limiting the peak value of electric current that flows at the time of switching so that a portion of the apparatus at which the electric current is concentrated is not broken.

The charge amplifier IC 233 provided on the TAB film includes a multiplicity of charge amplifiers 233a, a multiplicity of sample-holds (S/H) (sample-hold circuits) 233b and a multiplexer 233c. The multiplicity of charge amplifiers 233a and the multiplicity of sample-holds (S/H) 233b are connected to respective elements 215a of the solid-state detector 241. The multiplexer 233c multiplexes signals output from each of the sample-holds 233b. Electric current flowing out of the solid-state detector 241 is converted into a voltage by each of the charge amplifiers 233a. Then, the voltage is sample-held by the sample-hold 233b at predetermined timing. The sample-held voltage corresponding to each element 415a is sequentially output from the multiplexer 233c in such a manner that the voltage is switched in the arrangement order of the elements 415a (corresponding to a part of main scan). Signals that have been sequentially output from the multiplexer 233c are input to a multiplexer 231c provided on the printed circuit board 231. Further, a voltage corresponding to each of the elements 415a is sequentially output from the multiplexer 231c in such a manner that the voltage is switched in the arrangement order of the elements 415a. Accordingly, main scan ends. The signals that have been sequentially output from the multiplexer 231c are converted into digital signals by an A/D conversion unit 231a, and the digital signals are stored in a memory 231b.

As the pre-exposure light source unit 260, a light source that can emit and extinguish light in short time, and of which the persistence of light is very low, is required. Therefore, in the present embodiment, an external-electrode-type rare-gas fluorescent lamp is utilized. Specifically, as illustrated in FIG. 5, the pre-exposure light source unit 260 includes a plurality of external-electrode-type rare-gas fluorescent lamps 261, a wavelength-selection filter 262 and a reflection plate 263. Each of the plurality of external-electrode-type rare-gas fluorescent lamps 261 extends toward the back side of the paper on which FIG. 5 is illustrated. The wavelength-selection filter 262 is inserted between the fluorescent lamps 261 and the solid-state detector 241. The reflection plate 263 is provided behind the fluorescent lamps 261 so that light output from the fluorescent lamps 261 is efficiently reflected toward the solid-state detector 241 side. The pre-exposure light should irradiate the entire area of the second conductive layer 415 of the solid-state detector 241. Therefore, a condensing means for condensing light is not particularly needed. However, it is desirable that the illumination distribution is small. Further, as the light source, a light source formed by two-dimensionally-arranged LED chips may be utilized instead of the fluorescent lamps.

The movement means 247 is formed by a linear motor (not illustrated) or the like. The movement means 247 moves the solid-state detector 241 back and forth between a radiography position and a readout position parallel to the light source unit 243.

It is not necessary that the flat panel detector is the solid-state detector, as described above. The flat panel detector may adopt a TFT readout method (please refer to Japanese Unexamined Patent Publication No. 2004-080749, Japanese Unexamined Patent Publication No. 2004-073256, or the like). In the TFT readout method, signal electric charges accumulated in a charge storage portion of a solid-state detection element are read out by scan-driving a TFT connected to the charge storage portion.

The dose detector 242 is set under the solid-state detector 241. As the dose detector 242, an AEC sensor is used, for example. In the AEC sensor, semiconductor detectors are arranged as sensors for measuring radiation doses. Alternatively, the radiation dose may be detected based on the dose of radiation with which the solid-state detector 241 is irradiated (alternatively, the dose detector may be a TFT-type flat panel detector). In the following description of the present embodiment, the AEC sensor will be adopted as the dose detector 242.

The control unit 27 includes an overlap-degree obtainment means 271, an exposure condition setting means 272, a movement position control means 273 and an irradiation dose control means 274. The overlap-degree obtainment means 271 obtains information representing the degree of overlap of anatomical structures of a subject. The exposure condition setting means 272 sets exposure conditions, such as a radiography angle of the radiation source 22, an interval of radiography (or a radiography position) and a radiation dose, based on the obtained information. The movement position control means 273 sends a signal to the radiation source movement means 221 so that the radiation source 22 is moved to a position that has been set based on the exposure condition. The irradiation dose control means 274 controls the tube voltage and the tube current applied to the radiation source 22 or the like based on the exposure condition.

The overlap-degree obtainment means 271 obtains information representing the degree of overlap of anatomical structures such as mammary glands and fat, included in a breast, based on a radiographic image obtained by the radiation image detector 241 in pre-exposure (the anatomical structures include diseased regions as well as normal tissues). For example, a mammary gland appears as a white area in the radiographic image. Therefore, if more mammary glands are included in the breast and the degree of overlap of the mammary glands is high, the whole image becomes whiter. Therefore, the degree of overlap of the mammary glands is obtained based on the pixel values of the radiographic image. Alternatively, the degree of overlap of the mammary glands may be obtained based on a radiographic image obtained at one of positions S1, S2, . . . , Sn.

Further, there is a tendency that the amount of mammary glands and the amount of fat are larger as the thickness of a breast is thicker. Therefore, the thickness of the breast maybe detected based on the position of the compression plate 210 that is compressing the breast. Then, the thickness of the breast may be used as the degree of overlap of anatomical structures.

The exposure condition setting means 272 sets, based on the degree of overlap, exposure conditions, such as a radiography angle for radiographing the breast, a radiography position (radiography interval) and the dose of radiation with which the subject is irradiated. The radiation source 22 moves and emits radiation toward the breast from a plurality of positions. Therefore, if the radiation dose at each of the plurality of positions is the same as the dose of radiation emitted in ordinary mammography, in which a single mammogram is obtained by radiographing the breast from a single position, the subject is exposed to a great amount (dose) of radiation. Therefore, the dose of each radiation is reduced as the number of times of radiography increases. For example, the radiation dose is determined so that the total amount of radiation to which the subject is exposed in tomosynthesis radiography becomes the same as the amount of radiation to which the subject is exposed in ordinary mammography. Specifically, if radiography of a small breast should be performed at 55 mAs in ordinary mammography, the value of 55 mAs is used as a standard value for cases in which the degrees of overlap are small. When tomosynthesis radiography is performed from 11 positions, radiation is emitted from each of the 11 positions at a dose of 5 mAs based on the standard value. Further, if radiography of a large breast should be performed at 88 mAs in ordinary mammography, the value of 88 mAs is used as a standard value for cases in which the degrees of overlap are large. Then, when tomosynthesis radiography is performed from 11 positions, radiation is emitted from each of the 11 positions at a dose of 8mAs based on the standard value.

Figure 3:
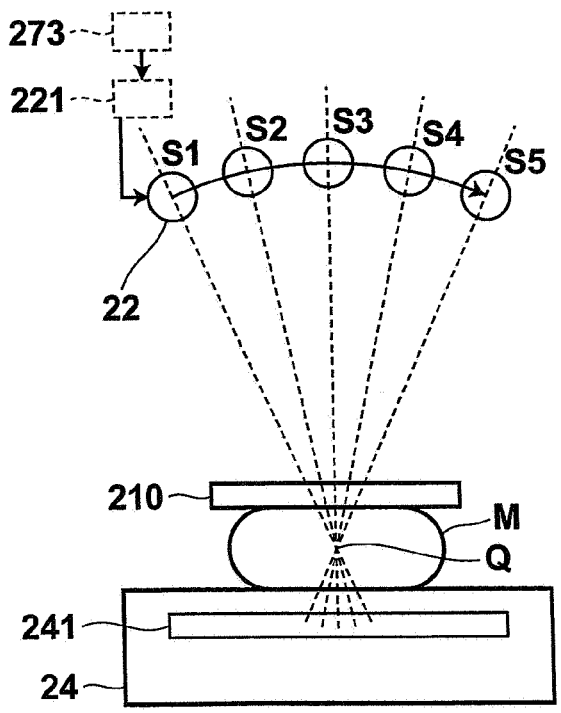
FIG. 3 is a frontal view of the arm of the mammography apparatus showing the rotation of the arm.

However, as the radiation dose becomes lower, an obtained radiographic image is affected more by the thickness of the breast. Further, as the distance (length) of travel of radiation passing through the breast becomes longer, an unclear radiographic image is formed. When the breast is radiographed, the distance of travel of radiation passing through each region of the breast differs depending on the direction of radiography of the breast. If radiation is emitted from the direction of the normal of the radiography surface of the radiography table 24, the distance of travel of radiation passing through the breast is the shortest in the vicinity of the center of the breast. The distance of travel of radiation passing through the breast becomes longer as a region is closer to the edge of the breast. Therefore, an image of a region in the vicinity of the center of the breast is clear, but an image of a region near the edge of the breast is not clear. Meanwhile, as illustrated in FIG. 3, when radiation is emitted from the vicinity of position S1, the distance (d1) of travel of radiation passing through the breast is shorter near the edge of the breast. Therefore, an image of a region near the edge of the breast, which is close to position S1, is clear. However, the distances (d2 and d3) of travel of radiation passing through the breast become longer as the radiation passes a region in the vicinity of the center of the breast or a region closer to the opposite edge of the breast (a region of the breast closer to position S5). Hence, unclear images are obtained.

Figure 10A:
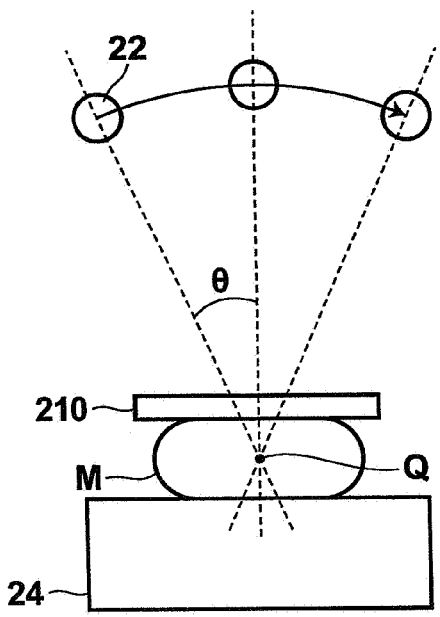
FIG. 10A is a diagram illustrating the range of radiography angles of the radiation source.
Figure 10B:
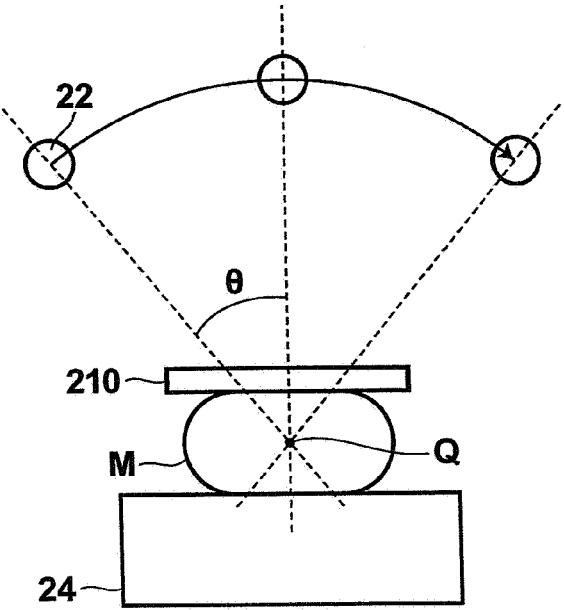
FIG. 10B is a diagram illustrating the range of radiography angles of the radiation source.

Normally, mammary glands included in a breast spread from a nipple. However, when the amount of mammary glands included in the breast is large, the mammary glands spread not only in the central part of the breast but in the whole breast in many cases. In such cases, it is desirable that clear images of regions near the edge of the breast are also obtained. Further, if the thickness of the breast is thick, the distance of travel of radiation passing through the breast is longer near the edge of the breast. Therefore, an unclear image of the region near the edge of the breast is obtained. Hence, if the amount of mammary glands included in the breast is small, or if the thickness of the breast is thin, it is sufficient if the radiation source 22 is moved in the vicinity of the center of the breast, as illustrated in FIG. 10A. However, if the amount of mammary glands included in the breast is large, or if the thickness of the breast is thick, it is necessary that a region near the edge of the breast as well as a region in the vicinity of the center of the breast is clearly radiographed. Therefore, it is insufficient if the radiation source 22 is moved only in the vicinity of the center of the breast. Hence, the exposure condition is set so that the range of movement of the radiation source 22 becomes longer, in other words, so that the range θ of radiography angles becomes wider, as illustrated in FIG. 10B. If the range of radiography angles is increased and radiation is emitted from a position close to the edge of the breast, the distance of travel of radiation passing through a region near the edge of the breast becomes shorter. Therefore, it is possible to obtain a radiographic image including a clear image of the region near the edge of the breast.

The movement position control means 273 controls the radiation source movement means 221 so that the radiation source 22 is moved to a radiography position based on the exposure condition that has been set by the exposure condition setting means 272. Further, the movement position control means 273 changes the direction of the radiation source 22 so that irradiation point Q is irradiated with radiation.

The irradiation dose control means 274 controls a tube voltage and a tube current as well as the radiation source 22 based on the exposure condition set by the exposure condition setting means 272.

Figure 11:
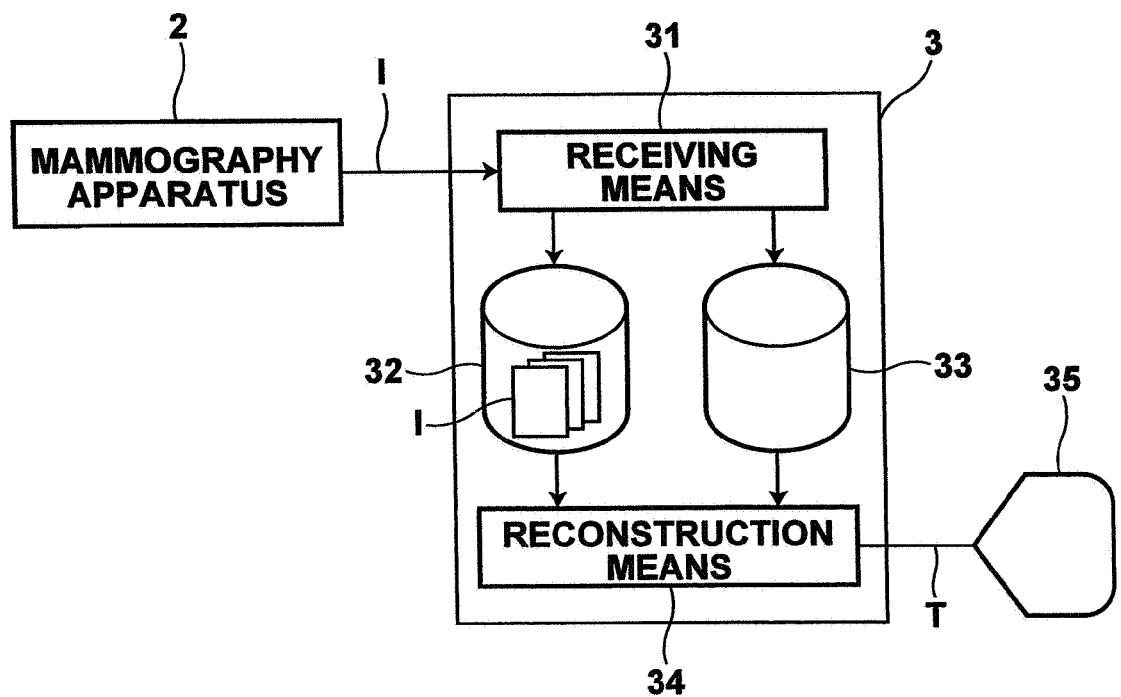
FIG. 11 is a diagram illustrating the configuration of a tomographic image formation apparatus.

FIG. 11 is a schematic diagram illustrating a tomographic image formation apparatus 3 of the present embodiment.

The tomographic image formation apparatus 3 includes a receiving means 31, a radiographic image storage means 32, an exposure condition storage means 33, a reconstruction means 34 and a display unit 35. The receiving means 31 receives data, such as a radiographic image obtained by the mammography apparatus 2 and an exposure condition. The radiographic image storage means 32 stores radiographic images I, and the exposure condition storage means 33 stores the exposure condition received from the mammography apparatus 2. The reconstruction means 34 produces tomographic image T by reconstructing the image from the plurality of radiographic images I. The display unit 35 displays the tomographic image T.

The radiographic image storage means 32 is a large-capacity storage apparatus, such as a hard disk. The radiographic image storage means 32 stores a plurality of radiographic images I obtained by the mammography apparatus 2. The plurality of radiographic images I are obtained at positions S1, S2, . . . , Sn by moving the radiation source 22 to each of the positions.

Figure 12:
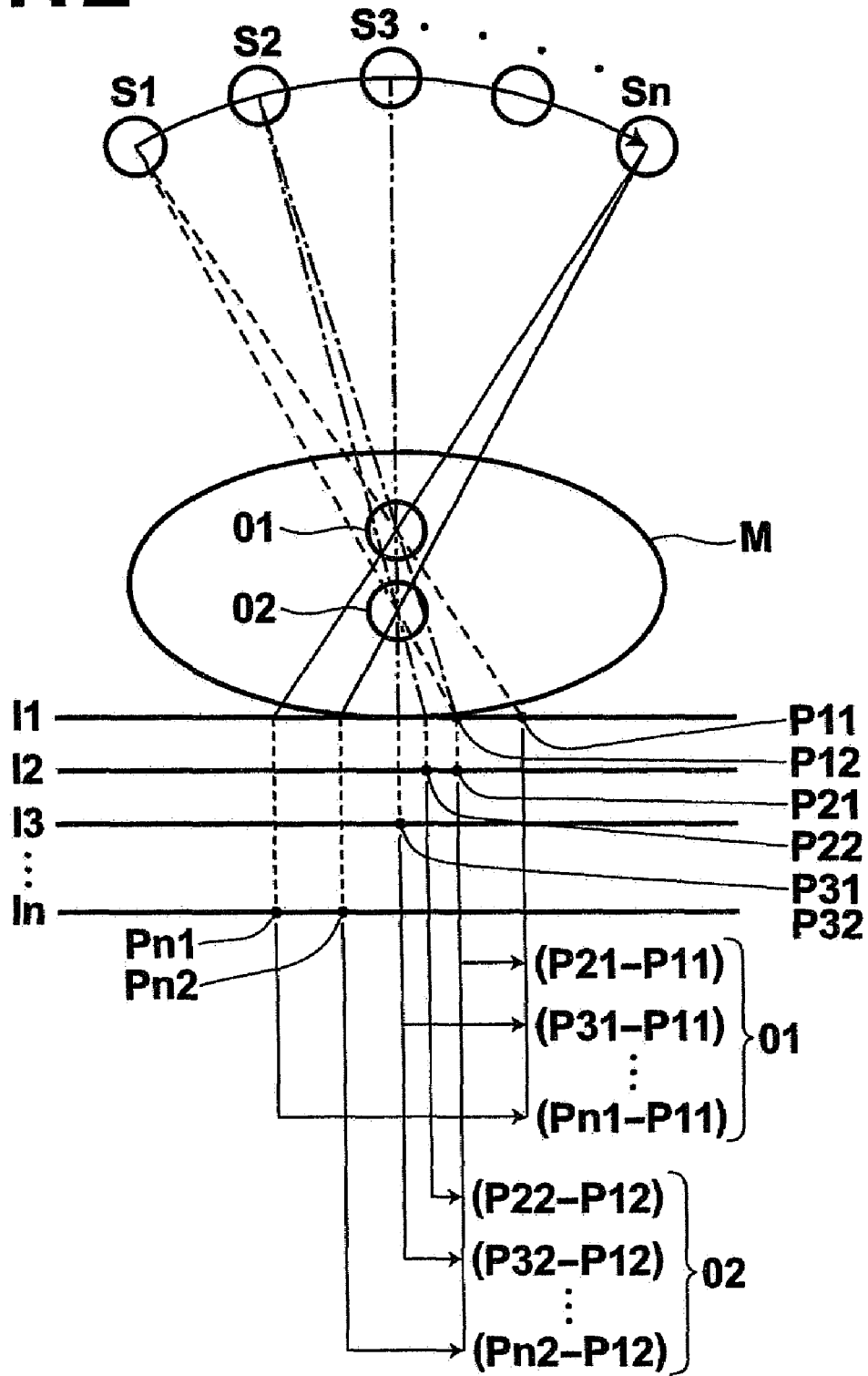
FIG. 12 is a diagram for explaining a method for reconstructing a tomographic image from radiographic images.

The reconstruction means 34 produces the tomographic image T from the plurality of radiographic images I obtained by radiography at positions S1, S2, S3, . . . , Sn. As illustrated in FIG. 12, if breast M is radiographed at different radiography angles from positions S1, S2, S3, . . . , Sn by moving the radiation source 22 to each of the positions, radiographic images I1, I2, I3, . . . , In are obtained at respective positions. For example, if objects (O1, O2), which are present at different depths, are projected from the radiation source at position S1, the objects are projected onto positions P11 and P12 in the radiographic image I1. If objects (O1, O2) are projected from the radiation source at position S2, the objects are projected onto positions P21 and P22 in the radiographic image I2. As described above, if projection is performed from different positions S1, S2, S3, . . . , Sn by moving the radiation source 22 to each of the positions, the object O1 is projected onto positions P11, P21, P31, . . . , Pn1 corresponding to the positions of the radiation source 22. Further, the object O2 is projected onto positions P12, P22, P32, . . . , Pn2 corresponding to the positions of the radiation source 22.

If a user wants to emphasize a cross-sectional plane on which the object O1 is present, the radiographic image I2 is moved by (P21-P11), the radiographic image I3 is moved by (P31-P11), . . . , and the radiographic image In is moved by (Pn1-P11). Then, the moved radiographic images are added together. Accordingly, a tomographic image in which a structure on the cross-sectional plane at the depth of the object O1 is emphasized is produced. If the user wants to emphasize a cross-sectional plane on which the object O2 is present, the radiographic image I2 is moved by (P22-P12), the radiographic image I3 is moved by (P32-P12), . . . , and the radiographic image In is moved by (Pn2-P12). Then, the moved radiographic images are added together. As described above, a tomographic image on a cross-sectional plane at each depth is obtained by adjusting the position of each of the radiographic image I1, I2, I3, . . . , In based on the position of the cross-sectional plane and by adding the radiographic images. Accordingly, a tomographic image on a cross-sectional plane at each depth is reconstructed.

Further, an object that is present at each depth is projected onto a different position of a radiographic image depending on a radiography angle. The radiography angle is an angle, at which radiation is emitted from the radiation source 22 at each position. Therefore, the reconstruction means 34 calculates, based on the exposure condition of the mammography apparatus 2 stored in the exposure condition storage means 33, the amount of movement (the distance of movement) of each of the radiographic images I1, I2, I3, . . . , In, and reconstructs a tomographic image.

As the display unit 35, it is desirable that a highly accurate display device, which is appropriate for diagnosis, is used.

The flow of operation for forming a tomographic image by radiographing a breast of a subject, using a tomographic image obtainment apparatus of the present embodiment, will be specifically described.

First, when a subject stands on the side of the mammography apparatus 2 to have a mammogram of her breast taken, an operator inputs a height of an arm corresponding to the height of the subject and a rotation angle of the arm corresponding to the size and shape of breast M at an operation unit 28, such as an operation panel. Then, the height and the angle of the arm 25 are adjusted, based on the input height and rotation angle, by the arm movement means 29. When MLO (mediolateral oblique) mammography is performed, the radiography table 24 is inclined by an angle within the range of 45 to 80 degrees from the horizontal direction so that the radiography table 24 and the pectoral muscle of the subject become parallel to each other (please refer to FIG. 13). Normally, the radiography table 24 is inclined by approximately 60 degrees during radiography. When CC (craniocaudal) mammography is performed, the radiography table 24 is kept in a horizontal direction, and the height of the radiography table 24 is adjusted.

Figure 13:
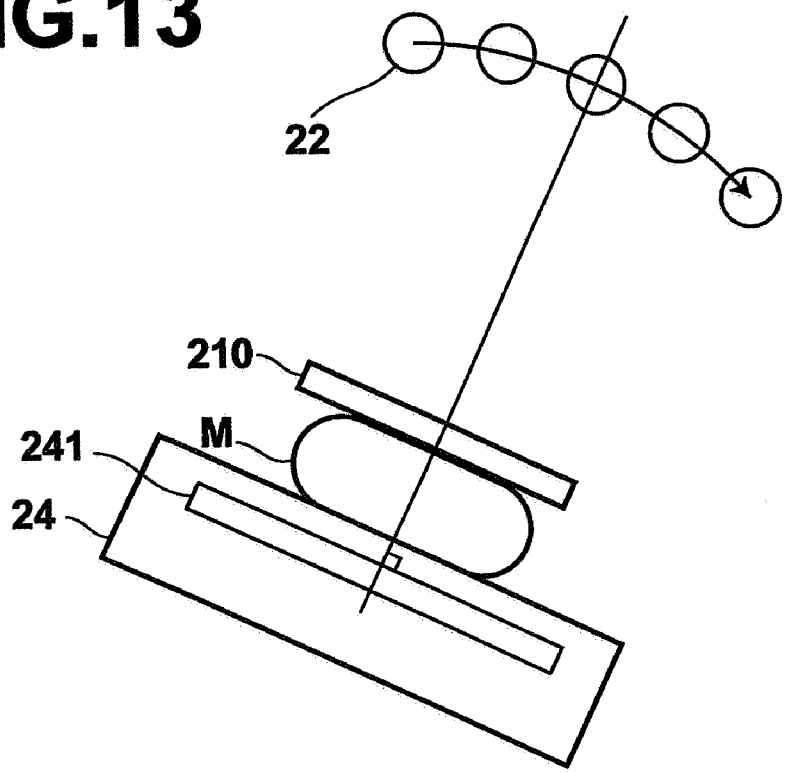
FIG. 13 is a diagram illustrating a breast and the range of radiography angles of the radiation source.

Further, the breast M is placed on the radiography surface of the radiography table 24 so that radiation emitted from the radiation source 22 at a radiography angle θ of 0 degree passes the central part of the breast M. Specifically, as illustrated in FIG. 13, the breast M is placed on the radiography surface of the radiography table 24 so that the radiation source 22 is positioned on a line that passes the central part of the breast M and extends in the direction of the nominal of the detection surface of the radiation image detector 241 in the radiography table 24.

The breast M is a three-dimensional object that has a substantial thickness. Therefore, if the breast M is radiographed without changing the shape of the breast M, a tumor does not appear in an obtained mammogram in some cases because the tumor is blocked by mammary glands, fat, blood vessels or the like. Therefore, when examination using mammography is performed, the breast M is evenly compressed with a compression plate 210 so that the breast M becomes thin. Accordingly, it becomes possible to capture an image of a shadow of even a small lump with low-dose radiation. Therefore, after the height and the angle of inclination of the radiography table 24 are adjusted in an appropriate manner for radiography, the breast M is compressed with the compression plate 210.

The operator inputs an instruction at the operation unit 28, such as an operation panel and a foot switch, so that the breast M is gradually compressed, checking the compression state of the breast M. The compression plate 210 is gradually moved down, based on the input, in the vertical direction of the arm 25 by the compression plate movement means 252. For example, the force of compression may be applied to the breast M so that the force is increased by 1 kg for each press of a foot switch. The foot switch is pressed until the thickness of the breast M becomes an appropriate thickness for radiography. Alternatively, the breast M may be gradually compressed when the compression plate 210 moves down and touches the breast M.

When compression of the breast M ends, the breast M is irradiated with radiation emitted from the radiation source 22 of the radiation storage unit 23, and radiography of the breast M starts.

First, pre-exposure is performed by emitting low-dose radiation from the radiation source 22 at the position with a radiography angle of 0 degree (this position is a position on a line extending from the detection surface of the radiation image detector 241 in the direction of the normal of the detection surface of the radiation image detector 241). Then, the radiation image detector 241 reads out a radiographic image obtained by the pre-exposure, and the overlap-degree obtainment means 271 obtains the degree of overlap of mammary glands based on the pixel values of the radiographic image.

Figure 14:
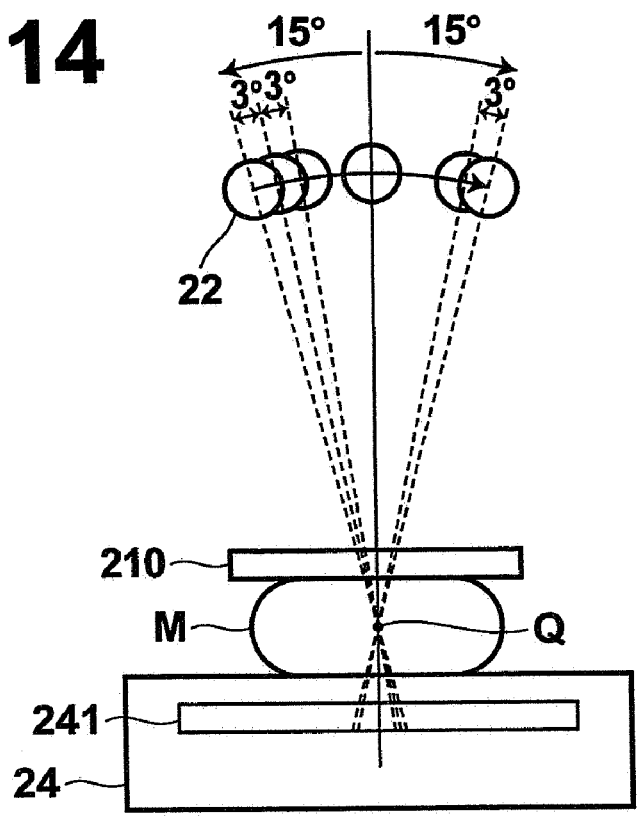
FIG. 14 is a diagram illustrating a relationship between a radiography angle and an interval of radiography.

If the breast is an ordinary breast, 11 mammograms are obtained by radiographing the breast, as illustrated in FIG. 14. The mammograms are obtained at radiography angles within the range of ±15 degrees with respect to a line extending in the direction of the normal of the radiation image detector 241 from the center of the breast. The mammograms are obtained at intervals of 3 degrees. However, if the degree of overlap is large, the range of the radiography angles is increased and radiography is performed. The exposure condition setting means 272 sets the range of radiography angles to ±20 degrees. The range of radiography angles is set, based on the degree of overlap, using a table, as illustrated in FIG. 15. The table illustrated in FIG. 15 shows correspondence between the degrees of overlap and radiography angles. Further, if the range of radiography angles is set to ±20 degrees, the interval of radiography is increased to 4 degrees, and 11 mammograms are obtained in total. The dose of radiation emitted at each position is set so that the total dose of radiation in tomosynthesis radiography becomes the same as the dose of radiation in ordinary mammography.

Figure 9:
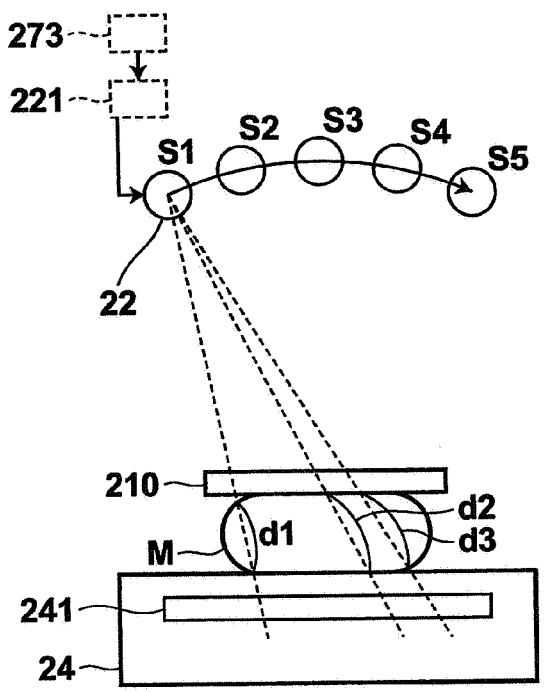
FIG. 9 is a diagram for explaining a relationship between the position of a radiation source and the distance of travel of radiation passed through a subject.

In the control unit 27, the movement position control means 273 controls the radiation source movement means 221 based on the set exposure condition (a radiography angle, the interval of radiography, a radiation dose or the like). Accordingly, the radiation source 22 is moved to position S1 on the extreme left (please refer to FIG. 9). Further, the radiation source 22 is directed toward radiation point Q. The irradiation dose control means 274 controls a tube voltage and a tube current so that the radiation source 22 emits radiation, of which the dose is based on the condition of exposure, to the breast. When the breast M is irradiated with radiation, a radiographic image is obtained from the radiation image detector 241. Then, the radiation source 22 is sequentially moved to positions S2, S3, . . . and radiation is emitted toward the irradiation point Q from each of the positions. Accordingly, radiographic images I are obtained. The obtained radiographic images I are sent from a transmission unit 261 to the tomographic image formation apparatus 3. Further, the exposure condition is sent to the tomographic image formation apparatus 3.

In the tomographic image formation apparatus 3, the receiving means 31 receives the radiographic images I and the exposure condition sent from the mammography apparatus 2. The radiographic images I are stored in the radiographic image storage means 32, and the exposure condition is stored in the exposure condition storage means 33.

The reconstruction means 34 reconstructs tomographic image T at each depth from the radiographic images I stored in the radiographic image storage means 32. The reconstruction means 34 reconstructs the tomographic image T based on the exposure condition stored in the exposure condition storage means 33. Then, the reconstructed tomographic image T is displayed at the display unit 35.

In the aforementioned embodiment, a case in which the radiation storage unit 23 is rotated with respect to the shaft C and the radiation source 22 is moved in an arc has been described. However, the radiation storage unit 23 may be kept in a fixed state and the radiation source 22 may be moved in an arc within the radiation storage unit 23.

Figure 16:
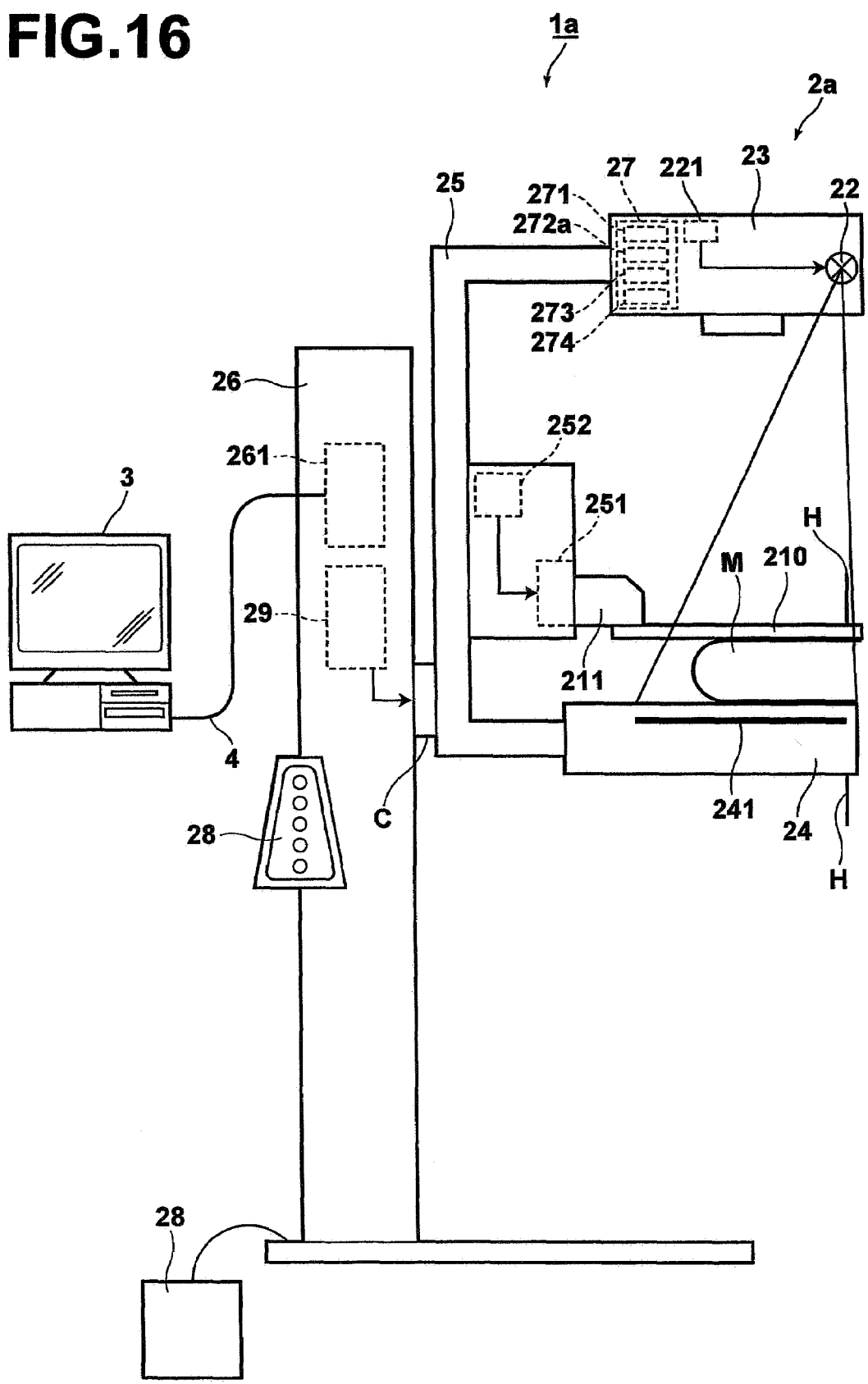
FIG. 16 is a diagram illustrating the configuration of a tomographic image obtainment apparatus in the second embodiment of the present invention.

Next, a second embodiment of the present invention will be described. In the present embodiment, if the thickness of a breast is thick, the number of times of radiography is increased to perform tomosynthesis radiography instead of increasing the range of radiography angles. FIG. 16 is a diagram illustrating the configuration of a tomographic image obtainment apparatus 1a according to the present embodiment. In the tomographic image obtainment apparatus 1a in the present embodiment, the same reference numerals are assigned to elements that are the same as those in the first embodiment, and detailed descriptions thereof are omitted. Only different elements will be described.

An exposure condition setting means 272a of a mammography apparatus 2a sets, based on the degree of overlap, exposure conditions, such as a radiography angle for radiographing breast M, a radiography position (the interval of radiography) and a radiation dose. In the present embodiment, when the thickness of the breast M is thick, the range of radiography angles is not increased. Instead, the exposure condition is set so that the number of times of radiography in tomosynthesis radiography is increased.

If a radiation dose is smaller, a mammogram is affected more by the thickness of the breast M. Further, if the distance of travel of radiation passing through the breast M is long in a region of the breast, an obtained image I of the region is not clear. If the distance of travel of radiation passing through the breast M is shorter in a region, a clearer image of the region is obtained. Specifically, an image of a region of the breast M that is close to each radiation position is clear. Therefore, it can be expected that if the interval of radiography is reduced, a larger area is clearly radiographed. Therefore, if the degree of overlap is large, the exposure condition is set so that the interval of radiography is reduced and the number of times of radiography is increased.

The flow of operation for forming a tomographic image by radiographing a breast of a subject will be described using a tomographic image obtainment apparatus of the present embodiment.

First, when a subject stands on the side of the mammography apparatus 2 to have a mammogram of her breast M taken, an operator adjusts the height and the angle of the arm at the operation unit 28, such as an operation panel, in a manner similar to the operation in the first embodiment. The height and the angle of the arm are adjusted in an appropriate manner for the subject. Then, the breast M is compressed with the compression plate 210. When compression is completed, radiation is emitted from the radiation source 22 in the radiation storage unit 23, and radiography of the breast M starts. First, pre-exposure is performed by emitting low-dose radiation from the radiation source 22 at the position with a radiography angel of 0 degrees. Then, a radiographic image obtained by pre-exposure is read out from the radiation image detector 241. The overlap-degree obtainment means 271 obtains the degree of overlap of mammary glands based on the pixel values of the radiographic image.

If the degree of overlap is small in breast M, 11 radiographic images are obtained by radiography, as illustrated in FIG. 17A, for example. In the example illustrated in FIG. 17A, radiography angles are within the range of ±30 degrees with respect to a line extending from the center of the breast M in the direction of the normal of the radiation image detector, and radiographic images are obtained at an interval of 6 degrees. However, if it is judged that the degree of overlap is large, exposure condition is set so that radiography is performed as illustrated in FIG. 17B. In FIG. 17B, the interval of radiography is reduced, and the number of times of radiography is increased. Specifically, exposure condition is set so that 21 radiographic images are obtained by radiographing at an interval of 3 degrees within the range of radiography angle of ±30 degrees. The exposure condition is set based on a table illustrated in FIG. 18. The table shows correspondence between the degree of overlap and the number of times of radiography.

Further, the exposure condition is set so that the total dose of radiation in tomosynthesis radiography becomes the same as a radiation dose in ordinary mammography. For example, if ordinary mammography is performed at 55 mAs when the size of breast M is small, this value is used as a standard value for a case in which the degree of overlap is small. Then, the dose of each radiation in tomosynthesis radiography is set to 5 mAs (55 mAs/11 times). Meanwhile, if the degree of overlap is large, the dose of radiation for a large breast M in ordinary mammography is used as a standard. If ordinary mammography for the large breast M is performed at 84 mAs, the dose of radiation in tomosynthesis radiography is set to 4 mAs because the number of times of radiography is increased to 21.

Tomosynthesis radiography is performed based on this exposure condition. The remaining features of the present embodiment are the same as those of the aforementioned embodiment. Therefore, detailed description will be omitted.

Figures 19, 20, 21:
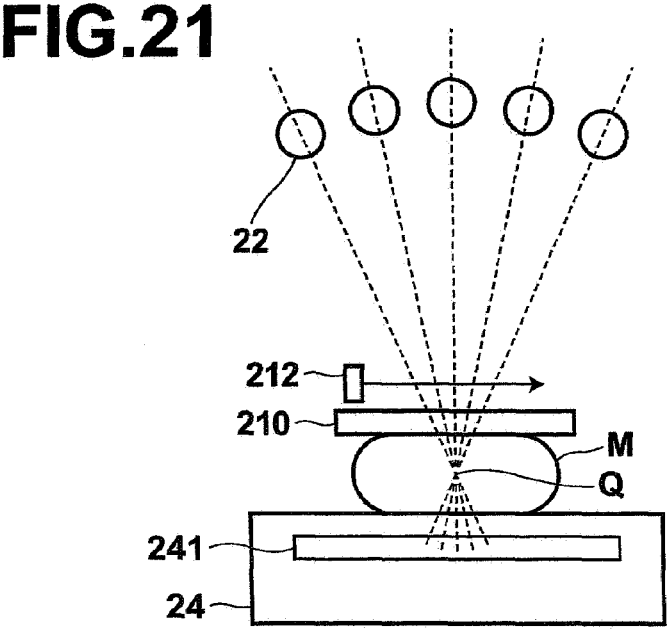
FIG. 19 is an example of a table showing correspondences between the degrees of overlap, the ranges of radiography angles and the numbers of times of radiography.
FIG. 20 is an example of a table showing correspondences between the thickness of a breast, the range of radiography angles and the number of times of radiography.
FIG. 21 is a diagram illustrating an example in which a probe, which scans a compression plate with ultrasound, is provided.

In the above description, a case in which one of the range of radiography angles from the radiation source 22 and the number of times of radiography is increased based on the thickness of the breast M has been described. However, both the range of radiography angles and the number of times of radiography may be increased. For example, as illustrated in FIG. 19, the exposure condition may be set so that the number of times of radiography is increased as the range of radiography angles is increased. When the number of times of radiography is increased, the dose of each radiation is reduced. The exposure condition is set so that the total dose of radiation to which the subject is exposed does not become large.

Further, in each of the aforementioned embodiments, a case in which the total dose of radiation in tomosynthesis radiography becomes the same as a radiation dose in ordinary mammography has been described. If the breast includes a substantial amount of mammary glands, or if the thickness of the breast is thick, the dose of each radiation may be set slightly higher so that a clear radiographic image is obtained in each radiation. In that case, the total dose of radiation in tomosynthesis radiography may be slightly higher than the dose of radiation in ordinary mammography.

Further, in each of the embodiments, a case in which the degree of overlap of anatomical structures is obtained based on the pixel values of a radiographic image obtained by performing pre-exposure has been described. However, the degree of overlap may be obtained based on the pixel values of a radiographic image I obtained by tomosynthesis radiography at a position with a radiography angle of 0 degree. In such a case, it is desirable that radiography is not performed twice at the same position with the radiography angle of 0 degree.

Further, if the thickness of the breast M is thick, the degree of overlap of mammary glands, fat or the like becomes higher in proportion to the thickness of the breast M. Therefore, the thickness of the breast M may be obtained based on the position of the compression plate 210, and the degree of overlap of anatomical structures may be obtained based on the thickness of the breast M. In such a case, a table as illustrated in FIG. 20 may be used to determine the exposure condition, such as the range of radiography angles and the number of times of radiography, corresponding to the thickness of the breast.

Alternatively, as illustrated in FIG. 21, a probe 212, which performs ultrasound scan by scanning the compression plate 210 with ultrasonic waves, may be provided. Then, an ultrasound image may be obtained, and the degree of overlap of anatomical structures, such as mammary glands, may be obtained based on the pixel values of the obtained ultrasound image.

Further, a distortion gauge may be provided on the radiography table 24, and the weight of breast M may be calculated based on the value indicated by the distortion gauge. Then, the weight of the breast M may be used as a value representing the degree of overlap of anatomical structures, such as mammary glands. Then, as illustrated in FIG. 22, the exposure condition, such as the range of radiography angles and the interval of radiography (the number of times of radiography), may be determined.

In the above description, a case in which the exposure condition in tomosynthesis radiography, such as the range of radiography angles and the interval of radiography, is changed based on the degree of overlap of the anatomical structures of a breast has been described. When the chest or stomach of a subject is radiographed, the exposure condition may be changed based on the density of a radiographic image obtained by pre-exposure. Alternatively, the exposure condition may be changed based on the size of the subject, such as the thickness and the weight of each region.

Further, the thickness and/or weight of a breast may be measured in advance before radiography, and the thickness and/or weight of the breast may be manually input to the mammography apparatus. When the chest or stomach of the subject is radiographed, the thickness and/or the weight of the region of the subject may be measured in advance before radiography, and the thickness and/or the weight may be manually input to a radiography apparatus.

In the aforementioned embodiments, a method for moving the exposure light source unit for readout has been adopted. However, if a solid-state light source such as an organic EL device, which emits highly bright light, is used, electrical readout becomes possible. Therefore, it is possible to shorten time for radiography. Alternatively, a flat panel detector using a TFT may be adopted.

As described above in detail, when tomosynthesis radiography is performed, if the exposure condition is changed based on the anatomical structures of a subject, it is possible to form a tomographic image including detailed information, which is appropriate for diagnosis.

What is claimed is:

1. A tomographic image obtainment apparatus, wherein a tomographic image is reconstructed from a plurality of radiographic images obtained by irradiating a subject with radiation from various directions, the apparatus comprising:

a radiation image detector for obtaining radiographic images of the subject;

a radiation irradiation unit placed so as to face the radiation image detector, the radiation irradiation unit moving to a plurality of positions and irradiating, at the plurality of positions, the subject placed on the radiation image detector with radiation from various directions;

an overlap-degree obtainment means for obtaining the degree of overlap of anatomical structures of the subject; and an exposure condition setting means for setting, based on the degree of overlap obtained by the overlap-degree obtainment means, a condition of exposure by the radiation irradiation unit at the plurality of positions to obtain the plurality of radiographic images.

2. A tomographic image obtainment apparatus, as defined in claim 1, wherein the overlap-degree obtainment means obtains the degree of overlap of the anatomical structures in the direction of the normal of a detection surface of the radiation image detector.

3. A tomographic image obtainment apparatus, as defined in claim 1, wherein the exposure condition setting means sets the condition of exposure so that the range of movement of the radiation irradiation unit is increased if the degree of overlap is large.

4. A tomographic image obtainment apparatus, as defined in claim 1, wherein the exposure condition setting means sets the condition of exposure so that an interval between the plurality of positions to which the radiation irradiation unit moves is reduced if the degree of overlap is large.

5. A tomographic image obtainment apparatus, as defined in claim 1, wherein the overlap-degree obtainment means obtains the degree of overlap based on the pixel values of a radiographic image obtained by radiographing the subject on the radiation image detector.

6. A tomographic image obtainment apparatus, as defined in claim 1, further comprising:

an ultrasound image obtainment unit for obtaining an ultrasound image of the subject on the radiation image detector, wherein the overlap-degree obtainment means obtains the degree of overlap based on the pixel values of the ultrasound image of the subject on the radiation image detector.

7. A tomographic image obtainment apparatus, as defined in claim 1, wherein the overlap-degree obtainment means obtains the degree of overlap based on the thickness of the subject.

8. A tomographic image obtainment apparatus, as defined in claim 1, wherein the overlap-degree obtainment means obtains the degree of overlap based on the weight of the subject.

9. A tomographic image obtainment method, wherein a tomographic image is reconstructed from a plurality of radiographic images obtained by irradiating a subject with radiation from various directions, the method comprising the steps of:

obtaining the degree of overlap of anatomical structures of the subject in a direction of irradiation; and setting a condition of exposure of the subject based on the obtained degree of overlap.

* * * * *